US008608736B2

(12) United States Patent
Kaufmann et al.

(10) Patent No.: US 8,608,736 B2
(45) Date of Patent: Dec. 17, 2013

(54) STEERABLE CATHETERS AND METHODS FOR MAKING THEM

(75) Inventors: Ralf Kaufmann, Lorrach (DE); Stephen A. Leeflang, Sunnyvale, CA (US); Christian S. Eversull, Palo Alto, CA (US); Wolfgang Geistert, Rheinfelden (DE)

(73) Assignee: VascoMed GmbH, Binzen (DE)

( * ) Notice: Subject to any disclaimer, the term of this patent is extended or adjusted under 35 U.S.C. 154(b) by 0 days.

(21) Appl. No.: 13/561,027

(22) Filed: Jul. 28, 2012

(65) Prior Publication Data

US 2013/0046298 A1 Feb. 21, 2013

Related U.S. Application Data

(60) Provisional application No. 61/512,634, filed on Jul. 28, 2011.

(51) Int. Cl.
*A61B 18/18* (2006.01)

(52) U.S. Cl.
USPC .......................................... 606/41; 604/95.05

(58) Field of Classification Search
USPC ................... 606/32–45; 604/95.04–95.05
See application file for complete search history.

(56) References Cited

U.S. PATENT DOCUMENTS 5,971,983 A * 10/1999 Lesh ................................ 606/41
2008/0161798 A1 * 7/2008 Podmore et al. .............. 606/41

FOREIGN PATENT DOCUMENTS

| EP | 0842673 | 5/1998 |
|----|---------|--------|
| WO | 00/06242 | 2/2000 |
| WO | 02/30310 | 4/2002 |
| WO | 03/037416 | 5/2003 |
| WO | 2005/081202 | 9/2005 |

OTHER PUBLICATIONS

Notification of Transmittal of the International Search Report and the Written Opinion of the International Searching Authority, International Search Report and Written Opinion of the International Searching Authority for PCT/US2012/048748, dated Feb. 1, 2013 (10 pages).

* cited by examiner

*Primary Examiner* — Linda Dvorak
*Assistant Examiner* — Amanda Scott
(74) *Attorney, Agent, or Firm* — Buchanan Ingersoll & Rooney PC

(57) ABSTRACT

Apparatus are provided for performing a procedure within a patient's body that include a tubular member including proximal and distal ends, a central axis or region extending therebetween, and a distal portion extending distally from an intermediate portion to the distal end. One or more accessory lumens and a steering element lumen extend between the proximal and distal ends, the steering element lumen offset from the central region within the distal portion such that a steering plane intersects the steering element lumen and the central axis. The distal portion includes a core member extending between the intermediate portion and the distal end, and stabilization elements embedded in the core member adjacent the accessory lumen and defining a stabilization plane that intersects the steering plane at a location offset from the central region, e.g., closer to the accessory lumen than the steering element lumen.

34 Claims, 5 Drawing Sheets

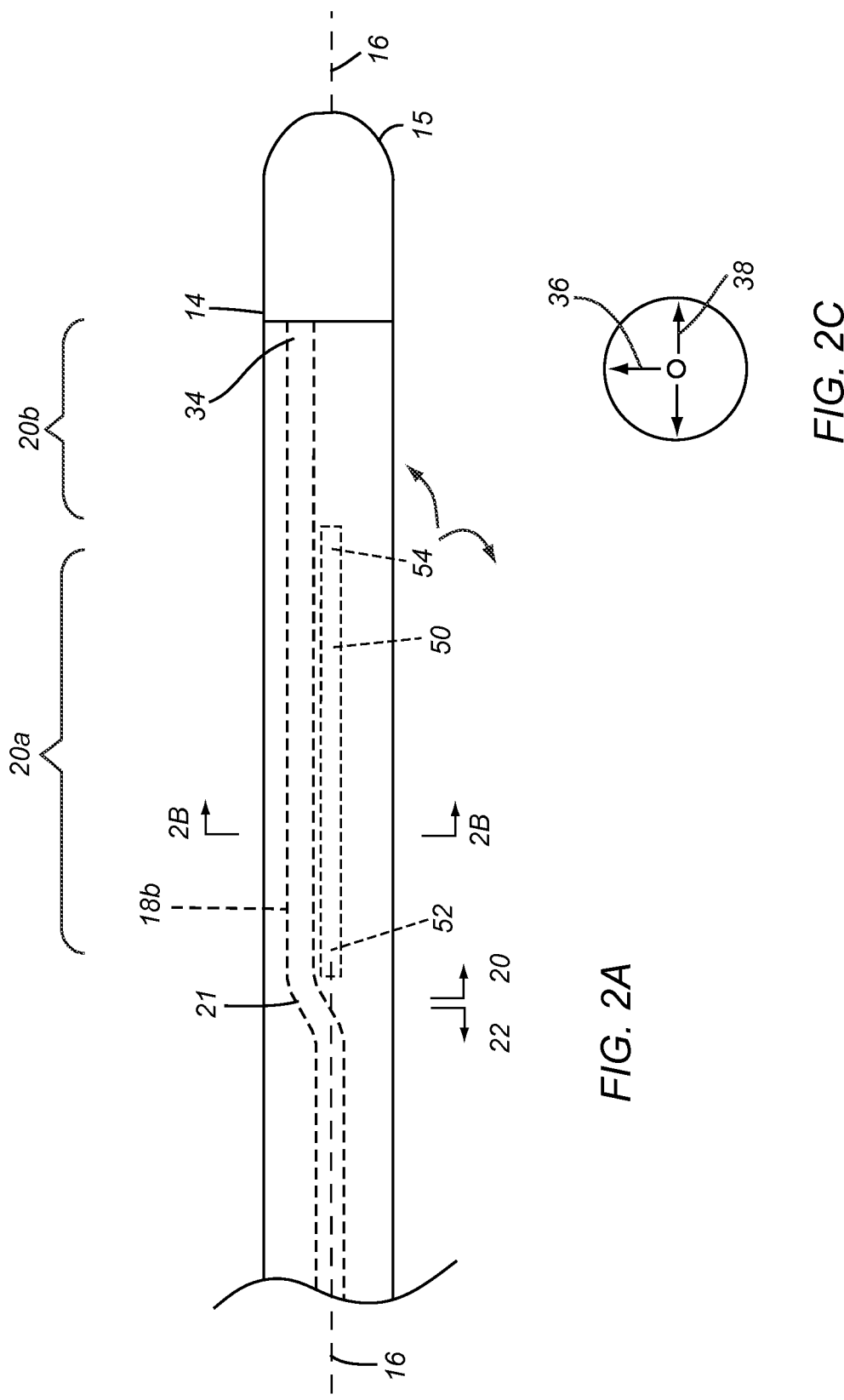

STEERABLE CATHETERS AND METHODS FOR MAKING THEM

RELATED APPLICATION DATA

This application claims benefit of provisional application Ser. No. 61/512,634, filed Jul. 28, 2011, the entire disclosure of which is expressly incorporated by reference herein.

FIELD OF THE INVENTION

The present invention relates generally to catheters, sheaths, or other tubular devices including steerable portions, and, more particularly, to steerable catheters, sheaths, or other tubular devices configured to deflect substantially in a predetermined plane, and to methods for making them.

BACKGROUND

Elongate tubular devices, such as diagnostic or treatment catheters or sheaths may be provided for introduction into a patient's body, e.g., the patient's vasculature or other body lumens. For example, a catheter may have a distal portion configured to be introduced into a body lumen and advanced to one or more desired locations within the patient's body by manipulating a proximal end of the catheter.

To facilitate introduction of such a catheter, one or more wires, cables, or steering elements may be provided within the catheter, e.g., that are coupled to the distal portion and may be pulled or advanced from the proximal end to deflect the distal portion. For example, a steering element may be provided that is intended to deflect the distal portion within a predetermined plane. However, the distal portion may deflect laterally out of the predetermined plane, e.g., due to anatomy encountered and/or other conditions.

Therefore, there is a need for apparatus that may enhance lateral stability of the steerable portions of catheters, sheaths, and other tubular devices.

SUMMARY

The present invention is directed to catheters, sheaths, or other tubular devices including steerable portions. More particularly, the present invention is directed to catheters, sheaths, or other tubular devices having steerable distal portions configured to deflect substantially in a predetermined plane, and to methods for making such catheters, sheaths, or other tubular devices.

In accordance with one embodiment, an apparatus is provided for performing a procedure within a patient's body that includes a tubular member including a proximal end, a distal end sized for introduction into a patient's body, a central region extending therebetween, and a distal portion extending distally from an intermediate portion to the distal end. At least one accessory lumen and a steering element lumen extend between the proximal end and the distal end, the steering element lumen offset from the central region within the distal portion, thereby defining a steering plane intersecting the steering element lumen and the central region. In an exemplary embodiment, the central region may correspond to the physical central axis of the tubular member, e.g., if the tubular member has a substantially circular or other symmetrical constructions about the central axis. Alternatively, the central region may correspond to a center of mass or other effective center of the tubular member, e.g., if the tubular member has an asymmetrical cross-section and/or a non-uniform density or material construction across its cross-section.

In one embodiment, the distal portion may include a core member extending between the intermediate portion and the distal end comprising a portion of the steering element lumen therein offset from and extending substantially parallel to the central region. Optionally, one or more additional layers, e.g., a reinforcement layer and/or an outer jacket, may be applied around the core.

One or more, e.g., a pair or plurality of, stabilization elements may be embedded in the core member, creating a stabilization plane extending between the stabilization elements that intersects the steering plane. In exemplary embodiments, the stabilization plane may intersect the steering plane, may be substantially perpendicular to the stabilization plane, may be aligned or intersect the central region, and/or may be offset from the central region, e.g., generally opposite the steering element lumen.

A steering element may be slidably disposed within the steering element lumen including a distal end fixed to the tubular member distal end and a proximal end coupled to an actuator on the tubular member proximal end such that, actuation of the actuator applies axial tension or compression to the steering element, thereby causing the distal portion to deflect substantially within the steering plane.

In one embodiment, the stabilization elements include a pair of elongate members, e.g., cables, extending partially along the length of the distal portion. The elongate members may have substantially circular cross-sections, oblong sections, e.g., defining a major axis extending substantially parallel to the stabilization plane, and the like. A first end of the elongate members may be disposed adjacent a transition region between the intermediate and distal portions, and a second end may be spaced apart proximally from a distal tip of the tubular member. In this embodiment, a region of the distal portion between the second ends and the distal tip may have greater flexibility than a region between the first and second ends of the elongate members, i.e., the region supported by the stabilization elements. Optionally, the elongate members may include surface features, which may enhance embedding the elongate members within the core and/or resist axial movement of the elongate members relative to the core.

In accordance with another embodiment, an apparatus is provided for performing a procedure within a patient's body that includes a tubular member including a proximal end, a distal end sized for introduction into a patient's body, a central axis extending therebetween, and a distal portion extending distally from an intermediate portion to the distal end. One or more accessory lumens and a steering element lumen may extend between the proximal end and the distal end, the steering element lumen offset from the central axis within the distal portion. The accessory lumen(s) may be disposed opposite the central axis from the steering element lumen within the distal portion, and a steering plane may intersect the steering element lumen and the central axis or other central region of the tubular member, and, optionally the accessory lumen(s).

The distal portion may include a core member extending between the intermediate portion and the distal end, and one or more stabilization elements embedded in the core member adjacent the accessory lumen and defining a stabilization plane that intersects the steering plane at a location closer to the accessory lumen than the steering element lumen. A steering element may be slidably disposed within the steering element lumen including a distal end fixed to the tubular member distal end and a proximal end coupled to an actuator on the tubular member proximal end. Actuation of the actuator may apply axial tension or compression to the steering element, thereby causing the distal portion to deflect substantially within the steering plane.

In an exemplary embodiment, the apparatus may be a mapping and/or ablation catheter, e.g., including one or more electrodes, sensors, and/or other elements on the distal portion. One or more wires or conductors coupled to the elements may extend through one or more accessory lumens, e.g., to the proximal end of the apparatus, which may be coupled to one or more connectors and/or other devices for operating and/or interacting with the elements.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 2A is a detail of the distal portion of the tubular device of FIG. 1.

FIG. 2C is a directional view illustrating the directions of deflection of the distal portion of the tublar device, such as that shown in FIG. 2A.

DETAILED DESCRIPTION OF THE EXEMPLARY EMBODIMENTS

Figure 1:
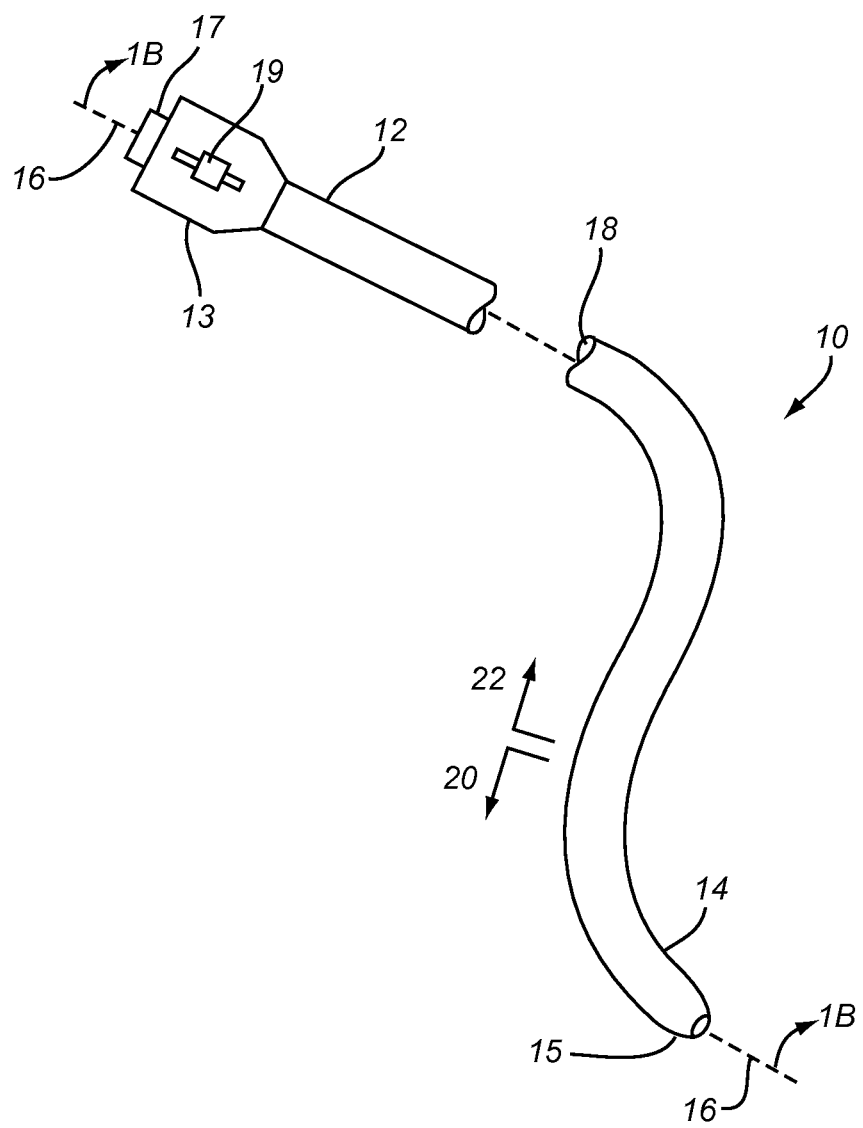
FIG. 1 is a perspective view of an exemplary embodiment of a tubular device, including one or more lumens extending between proximal and distal ends thereof, and including a steerable distal portion.

Turning to the drawings, FIG. 1 shows an exemplary embodiment of an apparatus 10 for accessing a body lumen (not shown) and/or for delivering one or more fluids, agents, and/or instruments (also not shown) into a patient's body. In exemplary embodiments, the apparatus 10 may be a guide catheter, a sheath, a procedure catheter, e.g., an imaging catheter, an ablation and/or mapping catheter, a balloon catheter, or other tubular device sized for introduction into a body lumen, such as a vessel within a patient's vasculature, a passage within a patient's gastrointestinal tract, urogenital tract, reproductive tract, respiratory tract, lymphatic system, and the like.

Figure 2B:
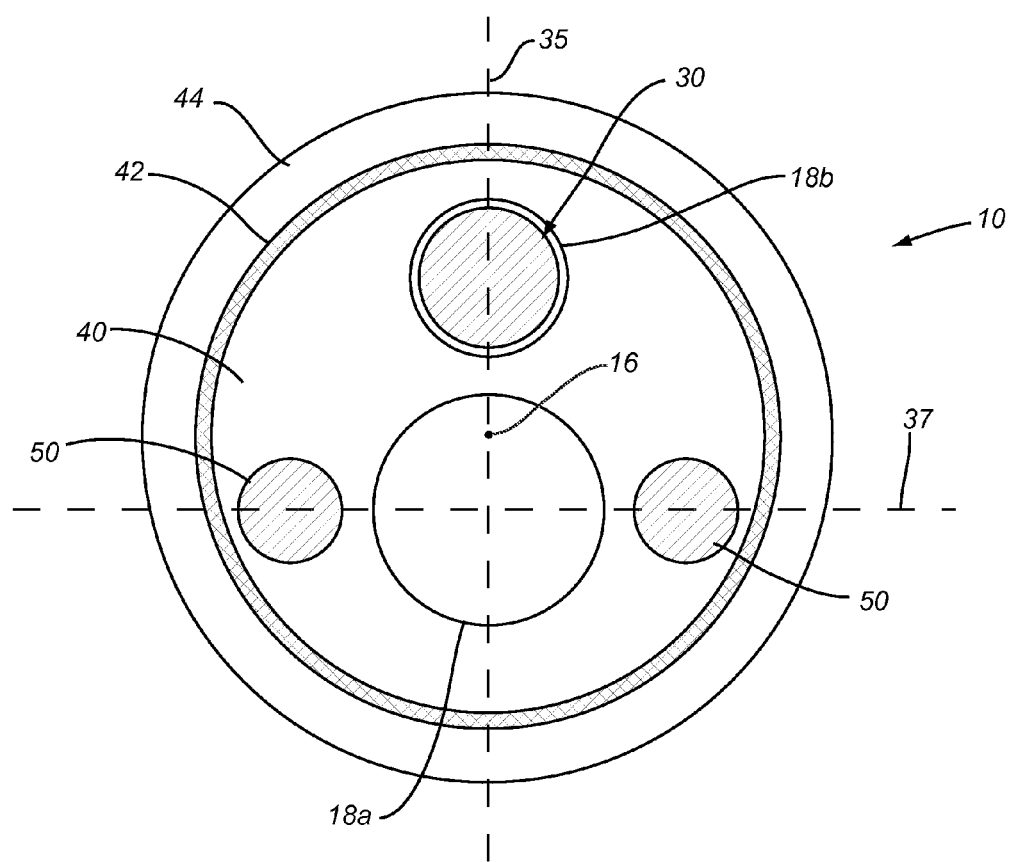
FIG. 2B is a cross-sectional view of the tubular device of FIG. 2A, taken along line 2B-2B, showing stabilization elements embedded within the distal portion to enhance lateral stability of the distal portion during deflection.

Generally, the apparatus 10 is an elongate tubular member including a proximal end 12, a distal end 14 sized for insertion into a body lumen, a central longitudinal axis 16 extending therebetween, and one or more lumens 18 extending between the proximal and distal ends 12, 14. For example, as shown in FIGS. 2A and 2B, the apparatus 10 may include an accessory lumen 18a sized for receiving or carrying one or more instruments or other elements (not shown) therethrough. In exemplary embodiments, the accessory lumen 18a may be sized for receiving or carrying a guide wire, procedure catheter, cardiac lead, needle, or other instrument (not shown), one or more wires or other conductors, one or more optical fibers, one or more tubes or accessory lumens, one or more mechanical elements, one or more sensors, and/or sized for delivering fluids or other flowable agents or materials therethrough. The accessory lumen 18a may communicate with an outlet 14a in the distal end 14 (e.g., as shown in FIG. 1) or may be enclosed within or adjacent the distal end 14, e.g., to isolate the accessory lumen 18a and/or elements carried therein from the environment outside the apparatus 10. In an exemplary embodiment where the apparatus 10 is an ablation and/or mapping catheter, the accessory lumen 18a may carry one or more wires or other conductors, thermocouple wires, tubes, and the like, e.g., coupled to electrodes or other elements (not shown) carried on the distal end 14.

In addition, a steering element lumen 18b may be provided with a pull wire or other steering element 30 therein, e.g., to bend or otherwise deflect a distal portion 20 of the apparatus 10, as described further below. Optionally, the apparatus 10 may include one or more additional lumens (not shown), e.g., additional steering element lumen(s) and/or accessory lumen(s) (not shown).

As shown in FIG. 2A, the distal end 14 may include a tapered, rounded, or otherwise shaped distal tip 15, e.g., to provide a substantially atraumatic tip and/or to facilitate advancement or navigation through various anatomy. In addition or alternatively, the distal end 14 may include one or more therapeutic and/or diagnostic elements, e.g., one or more balloons, stents, sensors, electrodes, ablation elements, thermocouples, steering mechanisms, imaging devices, helical anchors, needles, and the like (not shown), depending upon the particular intended application for the apparatus 10.

Optionally, as shown in FIG. 1, the proximal end 12 may include a handle or hub 13 and/or one or more ports, e.g., port 17 communicating with the accessory lumen 18a, or other respective lumens (not shown). Optionally, the port 17 may include one or more valves, e.g., a hemostatic valve (also not shown), which may provide a substantially fluid-tight seal, while accommodating insertion of one or more instruments or fluids into the accessory lumen 18a. In addition or alternatively, the handle 13 and/or proximal end 12 may include one or more connectors, such as luer lock connectors, electrical connectors, and the like, for connecting other devices (not shown) to the apparatus 10, such as syringes, displays, controllers, and the like (also not shown). In addition, the handle 13 may include one or more actuators, such as sliders, buttons, switches, and the like, e.g., for activating and/or manipulating components (also not shown) on the distal end 14 or otherwise operating the apparatus 10. For example, as shown in FIG. 1, an actuator 19 may be provided that is coupled to a proximal end of the steering element 30 (not shown), as described further below.

Generally, with particular reference to FIG. 2B, the apparatus 10 may include an inner core 40, e.g., surrounding or otherwise defining the lumen(s) 18, a reinforcement layer 42 surrounding or incorporated into the core 40, and an optionally outer jacket or layer 44 surrounding the reinforcement layer 42, extending at least partially between the proximal and distal ends 12, 14. The reinforcement layer 42 and/or outer jacket 44 may be attached to the core 40, e.g., by laminating, adhering, adhesive bonding, ultrasonic welding, reflowing or other heating, and the like, as described elsewhere herein. Optionally, one or more of the lumens 18, e.g., the accessory lumen 18a, may include an inner liner (not shown) or other material including an inner surface, and/or one or more coatings having desired properties.

Optionally, the core 40 may be formed from multiple sections and/or the reinforcement layer 42 and/or outer jacket 44 may include one or more sublayers (not shown). For example, the reinforcement layer 42 may include one or more reinforcing elements, e.g., wound in a braided or helical configuration around the core 40, and the outer jacket 44 may include one or more tubular layers surrounding the reinforcement layer 42 and/or between the reinforcement layer 42 and the core 40 (not shown). In exemplary embodiments, the reinforcement layer 42 may include one or more or a plurality of round or flat wires, filaments, strands, and the like, e.g., formed from metal, such as stainless steel, plastic, woven fibers, such as glass, Kevlar, and the like, or composite materials. For example, the reinforcement layer 24 may be configured to substantially transfer torsional forces between the proximal and distal ends 12, 14, e.g., to allow the apparatus 10 to be twisted from the proximal end 12 to rotate the distal end 14 about the longitudinal axis 16 within a patient's body. In addition, the reinforcement layer 42 may allow the distal end 14 of the apparatus 10 to be advanced or otherwise manipulated within a patient's body from the proximal end 12 without substantial risk of buckling and/or kinking.

Materials that may be used in the core 40 and/or outer jacket 44 include doped or undoped PEBAX, urethane, nylon (including nylon 6/6, nylon 11, nylon 12, PEBA) and engineered resins (including Zytel, Rilsan, Grilamid, Vestamid), polyethylene, polyvinylchloride, fluoropolymers (including PTFE, FEP, PFA, PVDF, THV, ETFE, ECFE), polyethylene terepthalate polyester, polyetheretherketone, polypropylene, silicone, natural and synthetic rubbers, polystyrene, polycarbonate, polymethylmethacrylate, and the like.

In one embodiment, one or more of the layers of the tubular member 10 may have a substantially homogenous construction between the proximal and distal ends 12, 14. Alternatively, the construction may vary along the length of the apparatus 10 to provide desired properties, e.g., between distal, intermediate, and proximal portions 20, 22, 24. For example, a proximal portion 24 of the tubular member 10 adjacent the proximal end 12 may be substantially rigid or semi-rigid, e.g., providing sufficient column strength to allow the distal end 14 of the apparatus 10 to be pushed or otherwise manipulated from the proximal end 12.

With particular reference to FIG. 2A, the distal portion 20 of the apparatus 10 may be steerable, i.e., may be curved or otherwise deflected substantially within a steering plane 35, e.g., as shown in FIG. 2B and described further below. The distal portion 20 extends between the intermediation portion 22 and the distal end 14 and includes one or more features to cause the distal portion 22 to bend or deflect in a desired manner, e.g., to bias the distal portion 20 to deflect substantially within the steering plane 35 and resist lateral bending out of the steering plane 35. As shown, the steering element lumen 18b is aligned with the central longitudinal axis 16 of the apparatus 10 within the intermediate portion 22 and is offset from the central longitudinal axis 16 within the distal portion 20, e.g., generally at transition region 21. Alternatively, the steering element lumen 18b may be offset from a center of mass or other central region of the distal portion 20. For example, for a circular cross-section core 40 having substantially uniform construction, the central axis 16 may correspond substantially to the center of mass of the distal portion 20. Alternatively, e.g., if the distal portion 20 has a non-circular or other asymmetrical cross-section and/or non-uniform material properties or construction across its cross-section, the center or mass or other central region intersecting the steering plane 35 may be offset at least somewhat from the physical central axis 16.

One or more pull wires, cables, fibers, threads, filaments, or other steering element 30 may be slidably received within the steering element lumen 18b, e.g., including a proximal end (not shown) coupled to the actuator 19 on the handle 13 (shown in FIG. 1) and extending through the intermediate portion 22, the transition region 21, and into the distal portion 20. A distal end 34 of the steering element 30 may be fixed or otherwise coupled to the distal end 14, e.g., to the component defining the distal tip 15, as shown in FIG. 2A. The steering element 50 may be formed from materials capable of substantially transferring any axial forces applied at the proximal end to the distal end 34, as is known in the art. Optionally, the steering element 50 may include a coating, e.g., PTFE or other lubricious material, an outer sleeve, e.g., formed from HDPE, PTFE, and the like, to reduce friction between the steering element 50 and the wall of the steering element lumen 18b.

During use, the actuator 19 may be activated, e.g., directed proximally or distally relative to the handle 13 and/or the proximal end 12, to apply an axial force to the steering element 30, e.g., tension (when the steering element 30 is pulled) or compression (when the steering element 30 is advanced). Within the intermediate portion 22, because the steering element lumen 18b and consequently the steering element 30 are generally aligned with the central axis 16, center of mass, or other central region of the intermediate portion 22, little or no bending moment is applied by this force. In addition or alternatively, the proximal and intermediate portions 24, 22 of the apparatus 10 may be constructed to prevent or minimize bending forces caused by actuation of the steering element 50.

At the transition region 21, the steering element lumen 18b is offset from the central axis 16, the center of mass, or other central region extending through the distal portion 20. Thus, an axial force on the steering element 30 creates a bending moment due to this offset, thereby causing the distal portion 22 to deflect substantially within a steering plane, e.g., within the plane of the view of FIG. 2A or in direction 36 shown in FIG. 2C.

To provide lateral stability within the distal portion, i.e., resisting lateral movement out of the steering plane 35 shown in FIG. 2B or in direction 38 shown in FIG. 2C, one or more stabilization elements 50 may be embedded within the core 40 of the distal portion 20, e.g., as shown in FIGS. 2A and 2B. In the exemplary embodiment best seen in FIG. 2B, a pair of stabilization elements 50 may embedded within the distal portion 20 adjacent one another to define a stabilization plane 37 therebetween, e.g., substantially parallel to the direction 38 shown in FIG. 2C. Alternatively, only one oblong shaped stabilization element or a plurality of stabilization elements may be embedded within the distal portion 20, e.g., similar to other embodiments herein and in application Ser. No. 61/512,634.

Figure 3A:
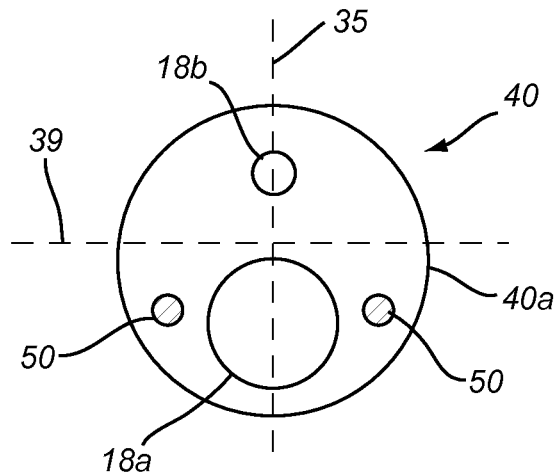
FIGS. 3A and 3B are cross-sectional views of alternative embodiments of distal portions of a tubular device, such as that shown in FIG. 1.

The stabilization elements 50 and the stabilization plane 37 may be aligned with the central axis 16, center of mass, or other central region of the distal portion 20, e.g., along a midline of the core 40, as shown in FIGS. 2A and 3A. Alternatively, the stabilization elements 50 and the stabilization plane 37 may be offset from the central axis 16, center of mass, or other central region of the distal portion 20, e.g., generally opposite the steering element lumen 18b and/or closer to the accessory lumen 18a than the steering element lumen 18b, as shown in FIG. 2B, and described further elsewhere herein.

In an exemplary embodiment, the stabilization elements 50 may be solid rods, cables, wires, flat wires, fibers, woven, twisted or braided threads or strands, or other elongate members, as shown in FIG. 2B, or hollow tubular members (not shown) having first and second ends 52, 54. Generally, the stabilization elements 50 have at least one of a tensile strength and a column strength between the first and second ends 52, 54 that is substantially greater than the tensile strength or column strength of the core 40. In an exemplary embodiment, each stabilization element 50 may be a section of twisted wire "cable," e.g., formed from metals, such as stainless steel, Nitinol, Elgiloy, and the like, polymers, such as nylon, PET, elastomers, PMMA, or other engineered materials, fibers, such as Kevlar, nomex, carbon, and the like, glass, or composite materials, which may resist elongation and/or compression. For example, stainless steel cable including multiple wires twisted around a single wire, e.g., 1×7 cable (six wires twisted around a core wire) having an overall outer diameter of about 0.012 inch (0.30 mm) may provide desired stability.

In the embodiment shown in FIG. 2A, the first ends 52 of the stabilization elements 50 may be disposed adjacent the intermediate portion 22 or transition region 21, and the second ends 54 may be spaced apart proximally from the distal end 14, e.g., by a predetermined distance from the location where the distal end 34 of the steering element 30 is fixed to the distal tip 15 or by a predetermined distance from the catheter tip e.g., between about five and fifty millimeters (5-50 mm), or to provide a desired ratio of the stabilized region and the more flexible region. Thus, in this configuration, the distal portion 20 may include a first region 20a between the transition region 21 and the second ends 54 of the stabilization elements 50, which may have a first set of flexibility or other bending characteristics, and a second region 20b between the second ends 54 and the distal tip 15, which may have a second set of flexibility or other bending characteristics. In exemplary embodiments, the second region 20b may provide a predetermined percentage of the deflectable distal portion 20 of the apparatus 10, e.g., between about ten and ninety percent (10-90%), or between about twenty and fifty percent (20-50%).

In an exemplary embodiment, it may be desirable to have the second region 20b, i.e., the region immediately adjacent the distal tip 15 to have greater flexibility, which may facilitate tracking and/or orienting the distal portion 20 within a patient's body, e.g., to facilitate advancement into branch vessels, through tortuous anatomy, and/or into organs, such as the heart, with minimal risk of damage to tissue. Different flexibilities between the first and second regions 20a, 20b may also provide other desired characteristics. For example, greater flexibility in the second region 20b may result in a smaller radius of curvature in the second region 20b than the first region 20a when the steering element 30 is actuated and/or may allow some lateral flexibility in the second region 20b.

Optionally, the stabilization elements 50 may include one or more features to enhance embedding and/or securing the stabilization elements 50 within the core 40, e.g., to prevent migration of the stabilization elements 50, e.g., when the distal portion 20 is deflected and/or lateral forces are applied. For example, the outer surface of a section of cable may include a plurality of helical hills and valleys, which may enhance embedding and/or prevent slipping of the cable within the core 40. In addition or alternatively, the surface of the stabilization elements 50 may be adapted, e.g., texturized, finished, perforated, and the like, to enhance interaction with the core 40, e.g., if the core 40 is molded or otherwise formed directly around the stabilization elements 50, as described further elsewhere herein.

Generally, it may be desirable to locate the stabilization elements 50 as far apart from one another and/or as close to the outer surface of the core 40, e.g., to enhance resistance to bending out of the steering plane 35. For example, as shown in FIG. 2B, the steering plane 35 may intersect the steering element lumen 18b, the central axis 16 (or other central region), and the accessory lumen 18a, e.g., intersecting the central axes of the lumens 18a, 18b. The stabilization elements 50 may be aligned on either side of the accessory lumen 18a, e.g., such that the stabilization plane 37 intersects the stabilization elements 50 and the accessory lumen 18a. However, the stabilization plane 37 may not intersect the central axis of the accessory lumen 18a, but may be offset away from the central axis 16 of the core 40. In addition or alternatively, the stabilization elements 50 may be located as far away from one another within the stabilization plane 37, e.g., close to the outer surface of the core 40, which may maximize the lateral "beam" created within the stabilization plane 37 by the stabilization elements 50.

As shown in FIGS. 2A and 3A, the stabilization elements 50 may be located generally opposite the steering element lumen 18b, e.g., with the stabilization elements 50 below a midline 39 of the core 40, and the steering element lumen 18b above the midline 39. Generally, it may be desirable to locate the stabilization elements 50 and/or the stabilization plane 37 as far from the steering element lumen 18b and/or steering element 18, e.g. to decrease resistance to bending in the steering plane 35 and/or improve the leverage of the steering element 18, and/or increase effective deflection generated by a given displacement of the steering element 18. Optimal positioning of the stabilization elements 50 may balance maximizing the distance between the stabilization elements 50, e.g. to maximize lateral stability, with maximizing the distance between the stabilization elements 50 and/or the stabilization plane 37 and the steering element 30, e.g., to maximize the ease of deflection of the distal portion 20. Thus, it is generally desirable to locate the stabilization elements 50 and/or stabilization plane 37 opposite the steering element lumen 18b as far as possible within or adjacent the core 40.

Thus, positioning the stabilization elements 50 opposite the steering element lumen 18b may facilitate deflection of the distal portion 20 and/or enhance resistance to movement out of the steering plane 35. Further, positioning the stabilization elements 50 away from one another may increase the bending moment or moment of inertia of the core 40 outside the steering plane 35.

Figure 3B:
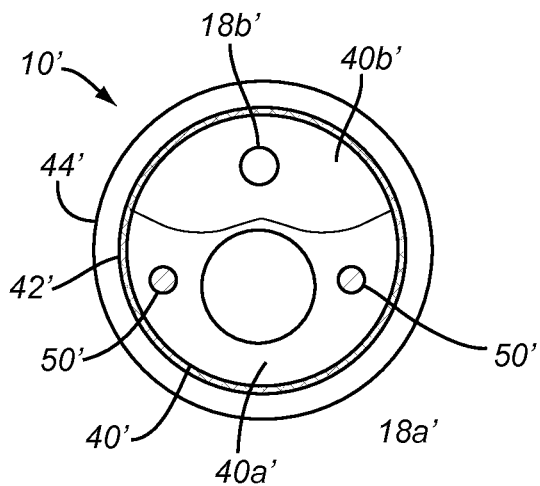

As shown in FIGS. 2B and 3A, the core 40 may be formed from a single, homogeneous material, as described elsewhere herein. Alternatively, as shown in FIG. 3B, the core 40 may be formed from multiple materials and/or sections having different mechanical properties. For example, as shown, the core 40' includes a first core section 40a' surrounding the stabilization elements 50' and/or accessory lumen 18a,' and a second core section 40b' surrounding the steering element lumen 18b.' For example, the material of the first core section 40a' may have greater stiffness, rigidity, durometer, and/or other properties than the second core section 40b.' The core sections 40a,' 40b' may be formed together or may be formed separately and attached together, as described elsewhere herein. In an exemplary embodiment, softer material surrounding or adjacent the steering element lumen 18b may be more easily compressed and/or extended, thereby facilitating bending of the distal portion 20 within the steering plane 35, while the stiffer material around or between the stabilization elements 50 may create a more effective "beam" within the stabilization plane 37.

Figure 4B:
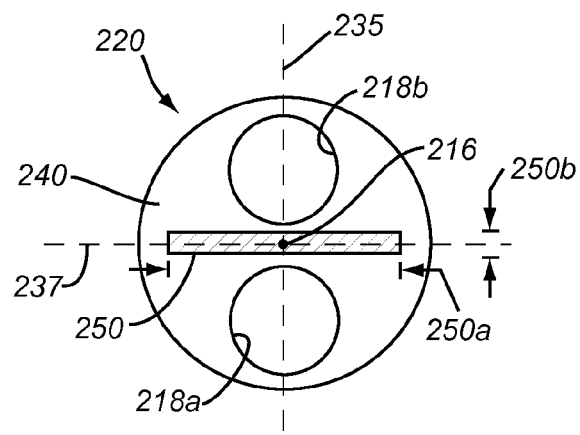
FIGS. 4A-4C are cross-sectional views of alternative embodiments of stabilization elements that may be embedded within the distal portion of a tubular device.
Figure 4A:
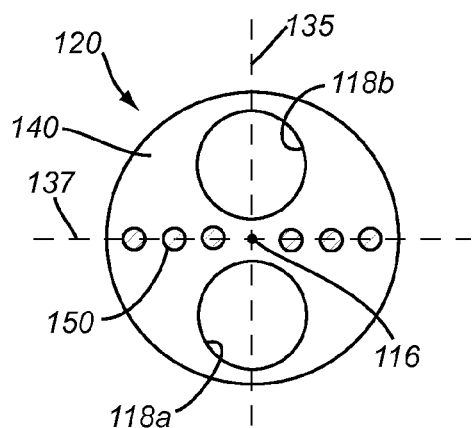
Figure 4C:
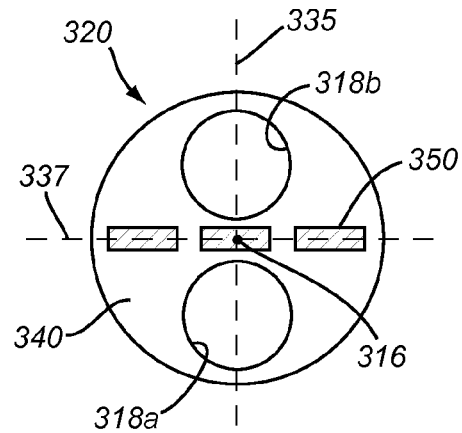

Turning to FIGS. 4A-4C, alternative embodiments of stabilization elements are shown that may be embedded or otherwise provided within the distal portion of a tubular device, such as any of the embodiments herein. For example, FIG. 4A shows a cross-section of a distal portion 120, which may be generally similar to that shown in FIG. 2A, except that more than two stabilization elements 150 are embedded within the core 140. As shown, seven (7) substantially circular cables or other elongate members 150 may be embedded within the core 140, lying linearly within a stabilization plane 137 substantially perpendicular to the desired steering plane 135 for the distal portion 120. Although the stabilization plane 137 is shown intersecting the central axis 116 of the distal portion 120, it will be appreciated that the stabilization elements 150 may be embedded offset from the central axis 116 (or other central region), e.g., opposite the steering element lumen 118b, to facilitate deflection of the distal portion 120 and/or enhance lateral stability, similar to other embodiments herein.

Turning to FIG. 4B, another cross-section of a distal portion 220 is shown, which may be generally similar to that shown in FIG. 2A, except that a single oblong stabilization element 250 is embedded within the core 240. As shown, the stabilization element 250 includes a major axis 250a that is substantially perpendicular to the steering plane 235, e.g., thereby defining a stabilization plane 237, and a minor axis 250b substantially parallel to the steering plane 235. The stabilization element 250 may have a substantially rectangular, oval, or other oblong cross-section, as desired and/or may include one or more surface features to enhance engagement with the core material, as described elsewhere herein.

Alternatively, as shown in FIG. 4C, a plurality of oblong stabilization elements 350 may be embedded in the core 340 aligned within a stabilization plane 337. As shown, three (3) oblong stabilization elements 350 are shown within the stabilization plane 337 intersecting the central axis 316 of the distal portion 320. Alternatively, the stabilization elements 350 (or 250) may be offset from the central axis 316 (or other central region), e.g., opposite the steering element lumen 318b. For example, a pair of oblong stabilization elements (not shown) may be provided on opposite sides of the accessory lumen 318a to facilitate deflection within the steering plane 335 and/or maximize lateral stability or resist deflection outside the desired steering plane 335, similar to other embodiments herein.

Figure 5:
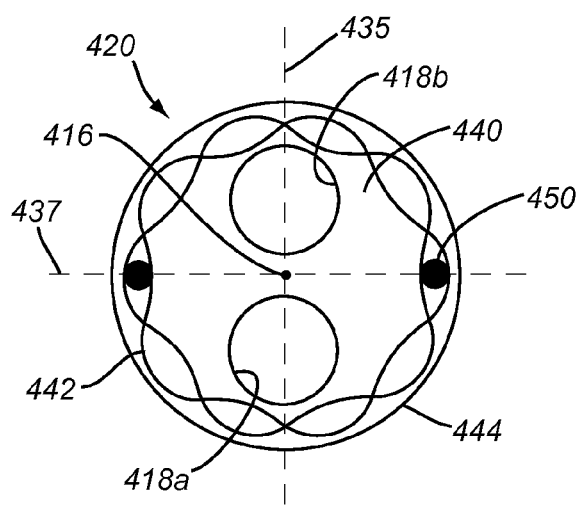
FIG. 5 is a cross-sectional view of another embodiment of a steerable distal portion including stabilization elements integrated into a reinforcement layer surrounding a core.

In another embodiment, shown in FIG. 5, a steerable distal portion 420 of an apparatus is shown that includes a pair of stabilization elements 550 embedded or otherwise incorporated within a reinforcement layer 442. For example, similar to other embodiments herein, the distal portion 420 may include an accessory lumen 418a and a steering element lumen 418b opposite a central axis 416, e.g., aligned with a steering plane 435 of the distal portion 420. However, rather than embed the stabilization elements 450 within the core 440, the stabilization elements 450 may be incorporated into the reinforcement layer 422, e.g., such that one or filaments or other elements of the reinforcement layer 422 are woven, wound, or otherwise applied at least partially around each stabilization element 550. As shown, the stabilization elements 450 may be aligned with one another within a stabilization plane 437, which may be aligned with the central axis 416 of the distal portion 420. Alternatively, similar to other embodiments herein, the stabilization elements 450 may be located offset from the central axis 416 (or other central region), e.g., closer to the accessory lumen 418a than the steering element lumen 418b, e.g., to facilitate deflection of the distal portion 420 within the steering plane 435 and/or increasing rigidity within the stabilization plane 437.

Any of the apparatus 10 herein may be incorporated into a variety of catheters, sheaths, or other medical devices. In exemplary embodiments, the apparatus 10 may have a length between about thirty and sixty five centimeters (30-65 cm), and an outer diameter between about four and ten French (4-10 Fr).

Returning to FIG. 2A, various methods may be used for manufacturing and/or assembling any of the embodiments described herein. In an exemplary method, the core 40 may be molded with the core material molded directly around the stabilization elements 50. For example, a mold may be provided within which the stabilization elements 50 may be suspended in the desired arrangement, e.g., defining a stabilization plane. One or more mandrels (not shown) may be supported relative to the stabilization elements 50 within the mold for respective lumens 18 to be formed in the core 40.

Core material, e.g., melted thermoset plastic or thermoplastic materials, may be introduced into the mold around the stabilization elements 50 and mandrel(s)s, e.g., to define the desired shape and/or length of the core 40 of the distal section 20 (or corresponding to the length of multiple distal sections, if desired). For example, with reference to the embodiment of FIGS. 2A and 2B, a pair of mandrels may be provided having sizes and/or shapes corresponding to the accessory lumen 18a and steering element lumen 18b. Once the core material is thermally, chemically, and/or otherwise set, the mandrel(s) may be removed to provide the lumen(s) 18 and the stabilization elements 50 may be embedded within the core 40. Alternatively, the core material may be introduced into the mold in separate layers, e.g., corresponding to the first and second sections 40a,' 40b' shown in FIG. 3B. For example, a first volume of core material having properties for the first section 40a' may be introduced into the mold and then a second volume of core material having properties for the second section 40b' may be introduced, e.g., after the first volume has at partially set to prevent mixing but fusing or otherwise attaching the sections together. In a further alternative, the first and second sections may be formed separately, e.g., by molding, extrusion, and the like, with the first section 40a' including the accessory lumen 18a' and the stabilization elements 50' and the second section 40b' including the steering element lumen 18b.' The separate sections 40,' 40b' may be attached to one another, e.g., by one or more of bonding with adhesive, fusing, heating and reflowing, by wrapping elements of the reinforcement layer 42 around the sections, and the like.

One or more layers may then be applied and/or formed around the core 40, e.g., a reinforcement layer 42 and/or outer jacket 44 to provide the distal portion 20. Alternatively, the core 40 may be attached to a core for the intermediate portion 22 and/or to the distal tip 15 before applying the reinforcement layer 42 and/or outer jacket 44. The intermediate and proximal portions 22, 24 may be formed using similar methods, e.g., by extrusion, hand lay-up, or other methods, but without the stabilization elements.

In a further alternative, as shown in FIG. 5, the core 440 may be molded or otherwise formed to include the lumens 418a, 418b without the stabilization elements 450. Instead, the stabilization elements 450 may be disposed adjacent the core 440 and one or more filaments or other reinforcing elements may be braided, wound, or otherwise applied around the core 440, thereby capturing the stabilization elements 450 therein. The outer jacket 444 may then be applied around the reinforcement layer 442. The layers may be attached together by bonding with adhesive, fusing, heating and reflowing the materials, and the like.

With continued reference to FIG. 2A, other elements or features may be provided on the distal portion 20, e.g., directly to the core 40 and/or with the reinforcement layer 42 and/or outer jacket 44. For example, for a mapping and/or ablation catheter, one or more electrodes (not shown) may be attached, mounted, or otherwise secured to the core 40 and/or outer jacket 44, which may be coupled to one or more wires or conductors introduced through the accessory lumen 18a.

A steering element 30 may introduced through the steering element lumen 18b, and a distal end 34 thereof may be coupled to a desired location within or adjacent the distal portion 20, e.g., to the distal tip 15, e.g., by bonding with adhesive, fusing, using one or more connectors (not shown), and the like. Thus, other than the fixed distal end 34, the steering element 30 may remain loose within the steering element lumen 18b from the distal portion 20 to the proximal end 12 of the apparatus 10. A proximal end of the steering element 30 may be coupled to an actuator 19 and/or handle 13 formed and attached to the proximal end 12 of the apparatus 10, as is known to those skilled in the art.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for performing a procedure within a patient's body, comprising:
   a tubular member comprising a proximal end, a distal end sized for introduction into a patient's body, a central region extending therebetween, and a distal portion extending distally from an intermediate portion to the distal end;
   at least one accessory lumen and a steering element lumen extending between the proximal end and the distal end, the steering element lumen offset from the central region within the distal portion, thereby defining a steering plane intersecting the steering element lumen and the central region;
   the distal portion comprising a core member extending between the intermediate portion and the distal end comprising a portion of the steering element lumen therein offset from and extending substantially parallel to the central region, and a pair of stabilization elements embedded in the core member creating a stabilization plane extending between the stabilization elements that intersects the steering plane; and
   a steering element slidably disposed within the steering element lumen comprising a distal end fixed to the tubular member distal end and a proximal end coupled to an actuator on the tubular member proximal end such that, actuation of the actuator applies axial tension or compression to the steering element, thereby causing the distal portion to deflect substantially within the steering plane.

2. The apparatus of claim 1, wherein the stabilization plane intersects the accessory lumen and does not intersect the central region.

3. The apparatus of claim 1, wherein the central region comprises one of a central axis of the distal portion and a center of mass of the distal portion, and wherein the stabilization plane intersects the central region.

4. The apparatus of claim 1, wherein the steering element lumen is aligned with the central region within the intermediate portion.

5. The apparatus of claim 1, wherein the steering element lumen is offset from the central region within the intermediate portion and the intermediate portion is constructed to resist axial compression such that axial forces applied to the steering element do not cause the intermediate portion to deflect substantially.

6. The apparatus of claim 1, wherein the stabilization plane is offset away from the central region in a direction opposite that of the steering element lumen.

7. The apparatus of claim 1, wherein the stabilization elements comprise elongate members including first ends disposed adjacent the intermediate portion and second ends spaced apart proximally from the distal end by a predetermined distance.

8. The apparatus of claim 1, wherein the stabilization elements have at least one of a tensile strength between the first and second ends that is substantially greater than the tensile strength of the core member and a column strength between the first and second ends that is substantially greater than the column strength of the core member.

9. The apparatus of claim 1, wherein the region of the distal portion between the second ends and the tubular member distal end has greater flexibility than a region of the distal portion between the first and second ends of the elongate members.

10. The apparatus of claim 1, wherein the elongate members comprise outer surfaces including features to prevent substantial migration of the elongate members within the core member.

11. The apparatus of claim 1, wherein the core member comprises a first core section surrounding the stabilization elements and a second core section surrounding the steering element lumen, the second core section having less stiffness than the first core section.

12. The apparatus of claim 1, further comprising one or more electrodes on the distal portion.

13. The apparatus of claim 12, further comprising one or more conductors extending through at least one accessory lumen from the tubular member proximal end to the distal portion and coupled to the one or more electrodes.

14. The apparatus of claim 1, wherein the stabilization elements have a length between about two and fifty centimeters (2-50 cm).

15. The apparatus of claim 1, wherein the tubular member distal end comprises a substantially atraumatic distal tip coupled to the core member.

16. The apparatus of claim 1, wherein the elongate members comprise sections of cable.

17. The apparatus of claim 1, wherein the elongate members comprise oblong cross-sections defining major axes extending substantially parallel to the stabilization plane.

18. The apparatus of claim 1, wherein the distal portion further comprises a reinforcement layer surrounding the core member and an outer jacket surrounding the reinforcement layer.

19. The apparatus of claim 18, wherein the reinforcement layer comprises one or more of a braided and a helical structure.

20. The apparatus of claim 1, further comprising one or more treatment or diagnostic elements on the distal portion.

21. An apparatus for performing a procedure within a patient's body, comprising:
  a tubular member comprising a proximal end, a distal end sized for introduction into a patient's body, a central axis extending therebetween, and a distal portion extending distally from an intermediate portion to the distal end;
  an accessory lumen and a steering element lumen extending between the proximal end and the distal end, the steering element lumen offset from the central axis within the distal portion, the accessory lumen disposed opposite the central axis from the steering element lumen within the distal portion such that a steering plane intersects the steering element lumen, the central axis, and the accessory lumen;
  the distal portion comprising a core member extending between the intermediate portion and the distal end, and one or more stabilization elements embedded in the core member adjacent the accessory lumen and defining a stabilization plane that intersects the steering plane at a location closer to the accessory lumen than the steering element lumen; and
  a steering element slidably disposed within the steering element lumen comprising a distal end fixed to the tubular member distal end and a proximal end coupled to an actuator on the tubular member proximal end such that, actuation of the actuator applies axial tension or compression to the steering element, thereby causing the distal portion to deflect substantially within the steering plane.

22. The apparatus of claim 21, wherein the stabilization plane is offset from the central axis opposite to the steering element lumen.

23. The apparatus of claim 21, wherein the steering plane is substantially perpendicular to the stabilization plane.

24. The apparatus of claim 21, wherein the stabilization plane intersects the accessory lumen.

25. The apparatus of claim 21, wherein the stabilization plane intersects the steering plane at a location that is further from the core member central axis than a radius of the accessory lumen.

26. The apparatus of claim 21, wherein the one or more stabilization elements comprise a plurality of stabilization elements disposed adjacent one another such that the stabilization plane intersects each of the stabilization elements.

27. The apparatus of claim 26, wherein the plurality of stabilization elements comprise a pair of stabilization elements disposed on opposite sides of the accessory lumen from one another.

28. The apparatus of claim 21, wherein the one or more stabilization elements comprise an oblong stabilization element defining a major axis and a minor axis, wherein the major axis extends substantially parallel to the stabilization plane.

29. An apparatus for performing a procedure within a patient's body, comprising:
  a tubular member comprising a proximal end, a distal end sized for introduction into a patient's body, at least one accessory lumen and a steering element lumen extending between the proximal end and the distal end; and a distal portion extending distally from an intermediate portion of the tubular member to the distal end, the distal portion comprising a core member extending between the intermediate portion and the distal end, a plurality of stabilization elements embedded in the core member creating a stabilization plane extending between the stabilization elements; and
  a steering element slidably disposed within the steering element lumen comprising a distal end fixed to the tubular member distal end and a proximal end coupled to an actuator on the tubular member proximal end such that, actuation of the actuator applies axial tension or compression to the steering element, thereby causing the distal portion to deflect substantially within a steering plane that is orthogonal to the stabilization plane.

30. The apparatus of claim 29, wherein the steering element lumen within the distal portion is located closer to a first side of the distal portion than a second opposite side of the distal portion, and wherein the stabilization elements are embedded within the core closer to the second side than the first side.

31. The apparatus of claim 30, wherein the tubular member further comprises an accessory lumen extending between the tubular member proximal and distal ends, and wherein the accessory lumen is located closer to the second side than the first side within the distal portion.

32. The apparatus of claim 31, wherein the plurality of stabilization elements comprise a pair of stabilization elements on either side of the accessory lumen such that the stabilization plane intersects the accessory lumen.

33. The apparatus of claim 29, wherein the steering plane that is substantially perpendicular to the stabilization plane.

34. An apparatus for performing a procedure within a patient's body, comprising:
  a tubular member comprising a proximal end, a distal end sized for introduction into a patient's body, at least one accessory lumen and a steering element lumen extending between the proximal end and the distal end; and a distal portion extending distally from an intermediate portion of the tubular member to the distal end, the distal portion comprising a core extending between the intermediate portion and the distal end, a reinforcement layer surrounding the core, and an outer jacket surrounding the reinforcement layer;
  a plurality of stabilization elements secured to the reinforcement layer creating a stabilization plane extending between the stabilization elements; and
  a steering element slidably disposed within the steering element lumen comprising a distal end fixed to the tubular member distal end and a proximal end coupled to an actuator on the tubular member proximal end such that, actuation of the actuator applies axial tension or compression to the steering element, thereby causing the distal portion to deflect substantially within a steering plane that is substantially perpendicular to the stabilization plane.

* * * * *